US012369600B2

(12) United States Patent
Asche et al.

(10) Patent No.: US 12,369,600 B2
(45) Date of Patent: Jul. 29, 2025

(54) COOLING COMPOSITION

(71) Applicant: Symrise AG, Holzminden (DE)

(72) Inventors: Jessica Asche, Holzminden (DE); Thomas Schoppmeier, Holzminden (DE); Jenny Weissbrodt, Holzminden (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 14/272,900

(22) Filed: May 8, 2014

(65) Prior Publication Data

US 2014/0335224 A1 Nov. 13, 2014

(30) Foreign Application Priority Data

May 9, 2013 (EP) .................................. 13 167 190

(51) Int. Cl.
| | |
|---|---|
| A23G 3/36 | (2006.01) |
| A23G 3/48 | (2006.01) |
| A23G 4/06 | (2006.01) |
| A23L 27/00 | (2016.01) |
| A23L 27/12 | (2016.01) |
| A23L 27/20 | (2016.01) |
| A61K 8/11 | (2006.01) |
| A61K 8/34 | (2006.01) |
| A61K 8/37 | (2006.01) |
| A61K 8/42 | (2006.01) |
| A61K 8/49 | (2006.01) |
| A61K 8/60 | (2006.01) |
| A61Q 11/00 | (2006.01) |
| B01J 2/04 | (2006.01) |

(52) U.S. Cl.
CPC ............. *A23G 3/36* (2013.01); *A23G 3/48* (2013.01); *A23G 4/06* (2013.01); *A23G 4/068* (2013.01); *A23L 27/00* (2016.08); *A23L 27/12* (2016.08); *A23L 27/203* (2016.08); *A23L 27/72* (2016.08); *A61K 8/11* (2013.01); *A61K 8/34* (2013.01); *A61K 8/37* (2013.01); *A61K 8/375* (2013.01); *A61K 8/42* (2013.01); *A61K 8/4973* (2013.01); *A61K 8/60* (2013.01); *A61Q 11/00* (2013.01); *B01J 2/04* (2013.01); *A23G 2200/00* (2013.01); *A23G 2200/14* (2013.01); *A23V 2002/00* (2013.01); *A61K 2800/244* (2013.01)

(58) Field of Classification Search
CPC ....... A23G 4/062; A23G 3/48; A23L 1/22016; A23L 1/222; A23L 1/2265
USPC .......... 426/3, 5; 564/170, 161; 514/621, 622
See application file for complete search history.

(56) References Cited

U.S. PATENT DOCUMENTS

| | | | | |
|---|---|---|---|---|
| 3,920,849 A | * | 11/1975 | Marmo ..................... | A23G 4/06 426/3 |
| 4,399,154 A | * | 8/1983 | Puglia ..................... | A23G 4/043 426/249 |
| 5,009,900 A | * | 4/1991 | Levine .................... | A23G 3/346 426/103 |
| 5,124,162 A | * | 6/1992 | Boskovic ................ | A23L 27/72 426/650 |
| 5,292,528 A | * | 3/1994 | Mori ...................... | A61K 8/416 424/401 |
| 2004/0013723 A1 | * | 1/2004 | Parikh .................... | A61K 8/11 424/456 |
| 2004/0202698 A1 | * | 10/2004 | Ramji .................. | A61K 9/0056 424/443 |
| 2005/0027017 A1 | * | 2/2005 | Surburg .................. | A23G 4/06 514/715 |
| 2006/0034894 A1 | * | 2/2006 | Lakkis ..................... | A23G 3/42 424/439 |
| 2007/0098842 A1 | * | 5/2007 | Wolf ....................... | A23G 4/06 426/3 |
| 2007/0148283 A1 | * | 6/2007 | Harvey ................... | A23G 3/36 426/3 |
| 2007/0231424 A1 | * | 10/2007 | Castro .................... | A23G 4/06 426/3 |

FOREIGN PATENT DOCUMENTS

| | | | |
|---|---|---|---|
| DE | 102008000265 | * | 10/2008 |
| DE | 102008000265 A1 | | 10/2008 |
| EP | 413539 A2 | | 2/1991 |
| EP | 1011643 A1 | | 6/2000 |
| EP | 2033688 A2 | | 3/2009 |
| EP | 2106704 A1 | | 10/2009 |
| WO | 97/16078 A1 | | 5/1997 |
| WO | 00/36931 A1 | | 6/2000 |
| WO | 2011/159935 A1 | | 12/2011 |

OTHER PUBLICATIONS

NPL Leffingwell JC et al. (A version from Leffingwell & Associates: in Perfumer and Flavorist, vol. 36, No. 6, pp. 24-31, 2011).*
Machine translation of FOR prior art Thomas W et al. (DE102008000265) is attached.*
NPL Peppermint oil (Retrieved on Oct. 28, 2021). (Year: 2021).*
Schober et al: "Flavor Release and Perception in Hard Candy: Influence of Flavor Compound-Flavor Solvent Interactions," J. Agric. Food Chem. Vol. 52, Issue No. 9, May 1, 2004, pp. 2628-2631.

(Continued)

*Primary Examiner* — Erik Kashnikow
*Assistant Examiner* — Bhaskar Mukhopadhyay
(74) *Attorney, Agent, or Firm* — POLSINELLI PC

(57) ABSTRACT

The invention is rooted in the food industry and relates to a composition which provides a physiologically cooling effect for imparting freshness in the used preparations and comprises 2 to 10% cooling agent (A), 0 to 35% alcohol (B), 55 to 95% hydrophobic compound (C). Furthermore, the invention relates to the production and use of the composition according to the invention in oral preparations, in particular chewing gums and sweets.

18 Claims, No Drawings

(56) References Cited

OTHER PUBLICATIONS

Potineni et al: "Influence of Flavor Solvent on Flavor Release and Perception in Sugar-Free Chewing Gum," J. Agric. Food Chem. vol. 56, Issue No. 9, May 1, 2008, pp. 3254-3259.

* cited by examiner

COOLING COMPOSITION

FIELD OF THE INVENTION

The invention is rooted in the food industry and relates to a composition which provides a physiologically cooling effect for imparting freshness in the used oral preparations and comprises 2 to 10% cooling agent (A), 0 to 35% alcohol (B) and 55 to 95% hydrophobic compound (C). Furthermore, the invention relates to the production and to the use of the cooling composition according to the invention in oral preparations, in particular chewing gums and sweets,

PRIOR ART

Chewing gums preferably consist of a water-insoluble chewable mass that remains in the mouth of the consumer even after long and intensive chewing. In addition to this chewable mass, chewing gums contain, for example, flavouring agents, sweeteners and substances having a physiological cooling effect that are released upon chewing and achieve a desired effect.

Particularly when using cooling agents, the challenge arises of creating not only the highest possible impact but also a cooling effect that lasts as long as possible. However, with known formulations it is often impossible or possible only to a very limited extent to create a particularly rapid and high impact and/or a particularly long-lasting cooling effect. The cooling effect thus often has a delayed onset and/or very quickly fades.

It is already known in the prior art that taste perception of the chewing gum can be improved and prolonged during chewing if the sweeteners are released in a controlled and gradual manner. Encapsulation agents are often used to delay an early and fast release of sweeteners in order to thereby control or delay the release of sweeteners. In terms of encapsulation materials, those suitable for food are possibilities, such as food-grade shellac, which can be applied to the chewing gum in various ways, for example by means of wet granulation, wax granulation, spray drying, spray-cooling, fluidised bed coating, coacervation and the like.

For example, EP1011643 B1 discloses the production of chewing gum. In this case, acyclic carboxamides are used as cooing agents, for example having an encapsulation agent, selected from among maltodextrin and acacia, to influence the cooling effect. This mixture is then added to a chewing gum formulation.

Generally, the encapsulation agents comprise a plurality of different food-grade encapsulation materials. However, these can be very expensive and are insufficiently effective to prolong the release of flavouring agents, sweeteners and cooling agents to the desired extent.

There is therefore a need to maintain, prolong, improve and enhance the sensorial properties—such as, in particular, the cooling effect or freshness with oral preparations, in particular with chewing gum and sweets—and to improve the impact thereof, during consumption.

The object of the present invention was to provide a composition which deploys a long-lasting and/or rapid-onset cooling effect in oral preparations, in particular chewing gum and sweets. Furthermore, the composition is used to enhance, prolong and improve the cooling effect of particular cooling agents. In addition, it was an object of the invention to incorporate this cooling composition into oral preparations, in particular into chewing gum or other confectionary. The object of the invention was thus in particular to provide a method for permanently incorporating this cooling composition into such oral preparations, in particular without thereby sacrificing or impairing the cooling effect.

DESCRIPTION OF THE INVENTION

The invention first relates to a composition having a cooling effect, comprising approximately 2 to approximately 15 wt. % cooling agent (A), 0 to approximately 35 wt. % alcohol (B), and approximately 55 to approximately 95 wt. % hydrophobic compound (C) which provides a physiological cooling effect for imparting freshness in the used oral preparations.

In this cooling composition the cooling agent brings about a cool sensation on the skin and on the (oral) mucosa. This sensation is created by an interaction of the cooling agents with thermoreceptors in the skin or (oral) mucosa. In this process the cooling agents bind to cold receptors of the skin or (oral) mucosa, thereby increasing the intracellular calcium concentration and triggering a nervous stimulus which creates a cold sensation in the body or is perceived as a cold feeling. TRPM8 is an example of such a receptor. This belongs to the group of cold and menthol receptors (also referred to as a cold-membrane receptor (CMR1)) or to the family of transient receptor potential ion channels. This receptor is specifically expressed in a special group of neurons and forms pores in the cell membrane (in each case 4 units come together to form a tetramer) which selectively allow for the passage of Ca2+ ions. The protein comprises 6 transmembrane domains and a cytoplasmatic C- and N-terminal. Lower temperatures (preferably 10-25° C.) stimulate this receptor, resulting in a signal transduction that is a interpreted as a cold feeling by the nervous system. The receptor was described for the first time in 2002 as a cold receptor in several publications (Peier A M et al, A TRP Channel that senses cold Stimuli and menthol. Cell. 2002 Mar. 8; 108(5):705-15; McKemy D D et al. Identification of a cold receptor reveals a general role for TRP Channels in thermosensation Nature 2002 Mar. 7; 416 (6876): 52-8; Zuker C S. Neurobiology: A cool ion Channel Nature 2002 Mar. 7; 416 (6876): 27-8).

Surprisingly, it has been found in the present invention that the addition of the above-mentioned composition not only has a cooling effect but also, due to the manner in which the composition is produced, the cooling effect sets in rapidly and with a high impact, is enhanced, improved and/or long-lasting. Oral preparations containing such a cooling composition may likewise have the stated advantages of the above-mentioned composition according to the invention.

Therefore, the invention also relates to a method for producing the cooling composition, characterised in that the cooling composition is encapsulated in a spray-granulation process, wherein the cooling agent (A) is completely dissolved in an upstream step in (B) and (C), so that a homogeneous mixture is produced, and the temperature being kept at 40° C. to 100° C., preferably at 45° C. to 80° C., more preferably at 50° C. to 70° C. and even more preferably at 40° C. to 50° C., for complete dissolution of (A). In the additional spray-granulation treatment process the temperature is kept at 35° C. to 65° C., preferably at 38° C. to 60° C., more preferably at 39° C. to 43° C., in order to prevent (A) from recrystalising, wherein the granulate particles obtained from the spray granulation having an average particle size of 0.3 mm to 0.9 mm, preferably of 0.4 mm to 0.8 mm, more preferably of 0.5 mm to 0.7 mm.

It has proven to be particularly advantageous for the ratio of cooling agent (A):alcohol (B):hydrophobic compound (C) to be 1:1:8, preferably 1:1.5:7.5, more preferably 1:3:6.

A concentration of 5 to 10 wt. % cooling agent (A), 10 to 90 wt. % alcohol (B) and 55 to 90 wt. % hydrophobic compound (C), preferably a concentration of 8 to 10 wt.-% cooling agent (A), 15 to 35 wt. % alcohol (B) and 60 to 80 wt. % hydrophobic compound (C), and especially of 9.5 to 10 wt.-% cooling agent (A), 25 to 30 wt. % alcohol (B) and 60 to 75 wt. % hydrophobic compound (C) is particularly effective and can be achieved according to the abovementioned production method, without then losing the cooling effect in oral preparations, in particular in chewing gum or sweets.

In a preferred embodiment, the concentration of cooling agent is 10 wt. %, of alcohol (B) is 30 wt % and of the hydrophobic compound (C) is 60 wt %.

The invention also relates to an oral preparation, comprising a cooling composition having the components (A), (B) and (C), as described above, the oral preparation preferably being a chewing gum or a sweet. The term "sweet" shall preferably be construed according to the invention to mean boiled and chewy sweets.

In a preferred embodiment, an oral preparation, which is a chewing gum, comprises a) 5-95 wt. % chewing gum base, b) 5-95 wt. % filler and sweetener, c) 0.1-15 wt. % flavouring agents and d) 0.4-2 wt. % a cooling composition according to the present invention, which provides a physiologically cooling effect for imparting freshness in the used oral preparations.

When examining the sensory properties of oral preparations, in particular chewing gum vis-à-vis conventional chewing gum, that is to say chewing gum without the combination of cooling agent (A), alcohol (B) and hydrophobic compound (C), which is produced according to the spray-granulation method described, no cooling effect materialises.

Cooling Agent A

Suitable cooling agents (A) are compounds of the type selected from the group consisting of acyclic carboxamide compounds and menthol compounds or mixtures thereof.

The combination of a plurality of active substance components, such as mixtures of a plurality of cooling agents, has the advantage that said components provide mutual synergetic support.

Menthol Compounds

Menthol compounds that can be used within the meaning of the invention are, for example, selected from the group formed by menthol methyl ether, menthone glyceryl acetal (FEMA GRAS[1] 3807), menthone glyceryl ketal (FEMA GRAS 3808), menthyl lactate (FEMA GRAS 3748), menthol ethylene glycol carbonate (FEMA GRAS 3805), menthol propylene gycol carbonate (FEMA GRAS 3806), menthyl-N-ethyl oxamate, monomethyl succinate (FEMA GRAS 3810), monomethyl glutamate (FEMA GRAS 4006), menthoxy-1,2-propanediol (FEMA GRAS 3784), menthoxy-2-methyl-1,2-propanediol (FEMA GRAS 3849) and the menthane carboxylic acid esters and amides WS-3, WS-4, WS-5, WS-12, WS-14 and WS-30 and mixtures thereof.

[1] FEMA stands for "Flavor and Extracts Manufacturers Association" and GRAS is defined as "generally regarded as safe". A FEMA GRAS label indicates that the thus characterised substance has been tested using standard methods and is deemed toxicologically safe.

All these substances are available on the market and can be obtained using standard organic is chemistry methods.

Monomethyl succinate (FEMA GRAS 3810) is a first important agent. This was patented by Brown & Williamson Tobacco Corp. back in 1963 (U.S. Pat. No. 3,111,127) and forms the subject matter of intellectual property rights U.S. Pat. Nos. 5,725,865 and 5,843,466 (V. Mane Fils) as a cooling agent. Both succinate and the similar monomenthyl glutarate (FEMA GRAS 4006) are important agents of monomenthyl esters based on di- and polycarboxylic acids:

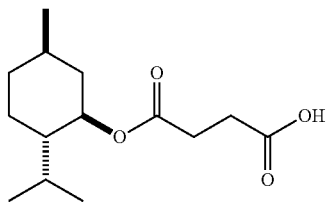

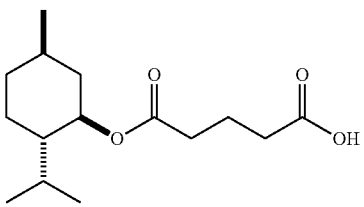

Examples of applications for these substances can be found in WO 2003 043431 (Unilever) and EP 1332772 A1 (IFF), for example.

The next important group of menthol compounds preferred within the meaning of the invention comprises carbonate esters of menthol and polyols, such as glycols, glycerols or carbohydrates, such as menthol ethylenglycol carbonate (FEMA GRAS 3805=Frescolat® MGC), menthol propylene glycol carbonate (FEMA GRAS 3784=Frescolat® MPC), menthol 2-methyl-1,2-propanediol carbonate (FEMA GRAS 3849) or the corresponding sugar derivatives:

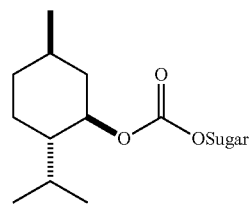

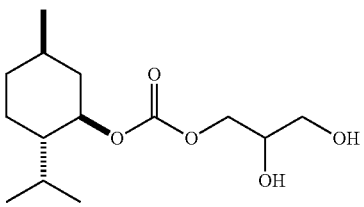

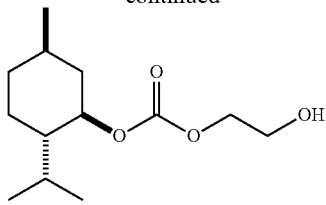

Menthol ethylene glycol carbonate

The use of this type of substance as a cooling agent for cigarettes forms, for example, the subject matter of U.S. Pat. No. 3,419,543 (Mold et al.) from 1968; application as a physiological cooling agent is claimed in DE 4226043 A1 (H&R).

Preferable within the meaning of the invention are the menthol compounds menthyl lactate (FEMA GRAS 3748=Frescolat® ML) and in particular menthone glyceryl acetal (FEMA GRAS 3807) or menthone glyceryl ketal (FEMA GRAS 3808), which is marketed under the name Frescolat® MGA.

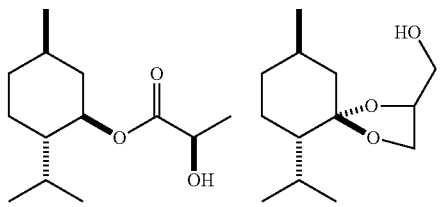

The former structure is obtained by esterifying lactic acid with menthol, which is obtained by acetalising menthone with glycerol (cf. DE 2608226 A1, H&R). This group of compounds also contains 3-(l-menthoxy)-1,2,propanediol, which is also known as cooling agent 10 (FEMA GRAS 3784, cf. U.S. Pat. No. 6,328,982, TIC), and 3-(l-menthoxy)-2-methyl-1,2,propanediol (FEMA GRAS 3849), which has an additional methyl group.

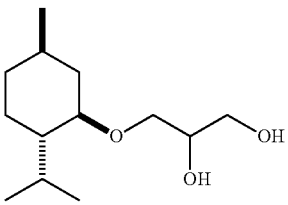

Cooling Agent 10

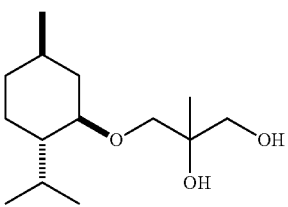

I-Menthoxy-2-methyl 1,2-propanediol

The 3-(l-menthoxy)-1,2,propanediol is produced, for example, starting from menthol according to the following diagram (cf. U.S. Pat. No. 4,459,425, Takagaso):

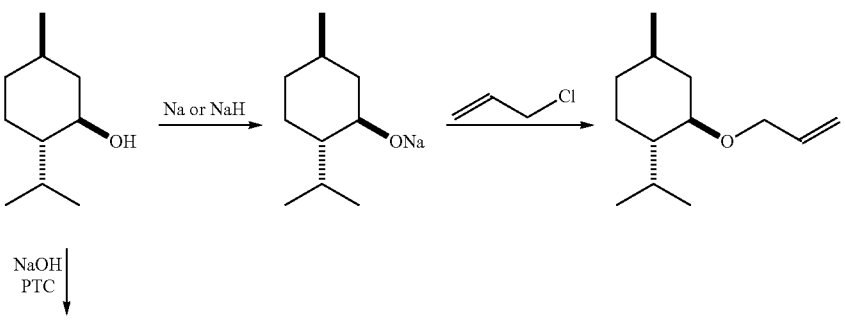

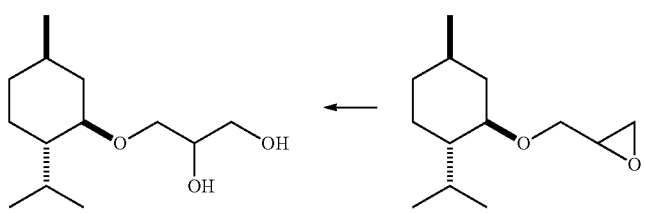

Alternative approaches, in which menthol is reacted with epichlorohydrin in the first step, are described in U.S. Pat. Nos. 6,407,293 and 6,515,188 (Takagaso). The following gives an overview of the preferred menthol compounds, which are distinctive on account of a CO-bond:

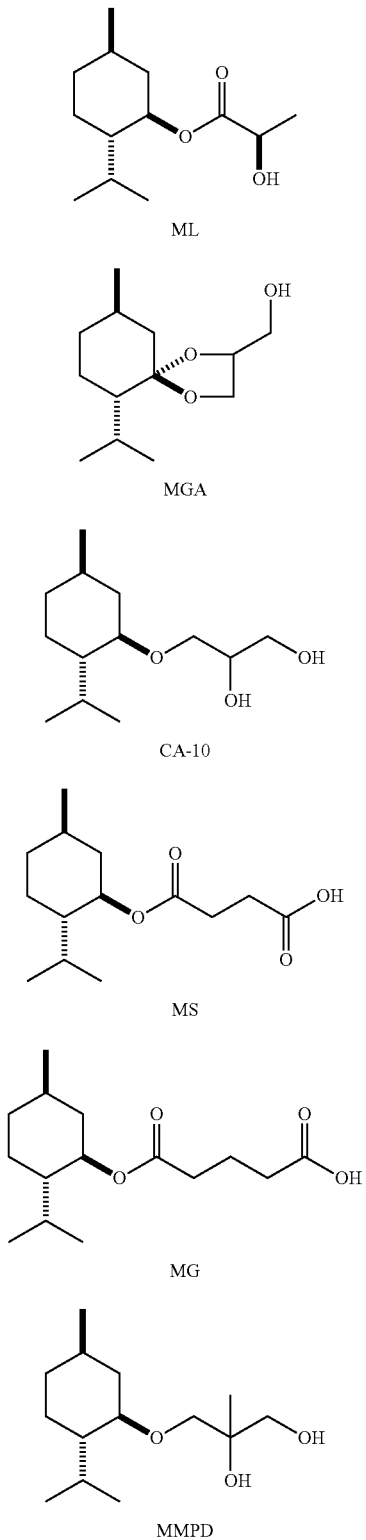

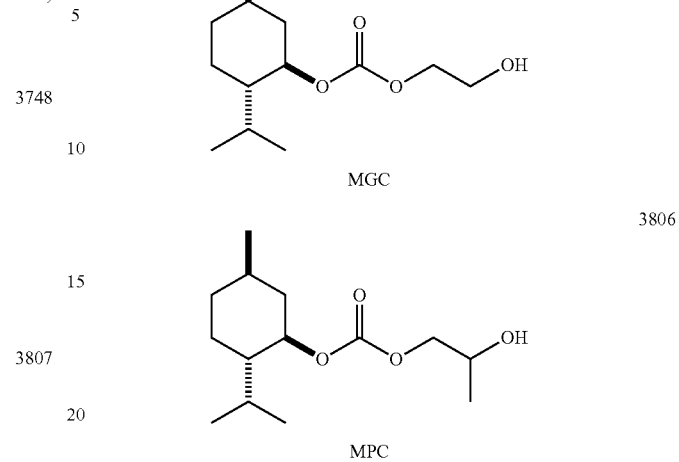

Menthone glyceryl acetal/ketal, menthyl lactate, menthol ethylene glycol carbonate and menthol propylene glycol carbonate have proved to be particularly advantageous among these substances and are sold by the applicant under the names Frescolat® MGA, Frescolat® ML, Frecolat® MGC and Frescolat® MPC.

In the 1970s, menthol compounds were developed for the first time which have a C—C bond in the third position and can also be replaced with a series of agents within the meaning of the invention. These substances are generally referred to as WS types. The parent substance is a menthol derivative in which the hydroxyl group is replaced with a carboxyl group (WS-1). All other WS types are derived from this structure, such as the species, which are also preferred within the meaning of the invention, of WS-3, WS-4, WS-5, WS-12, WS44, WS 23 and WS-30. The following two illustrations show the synthesis paths:

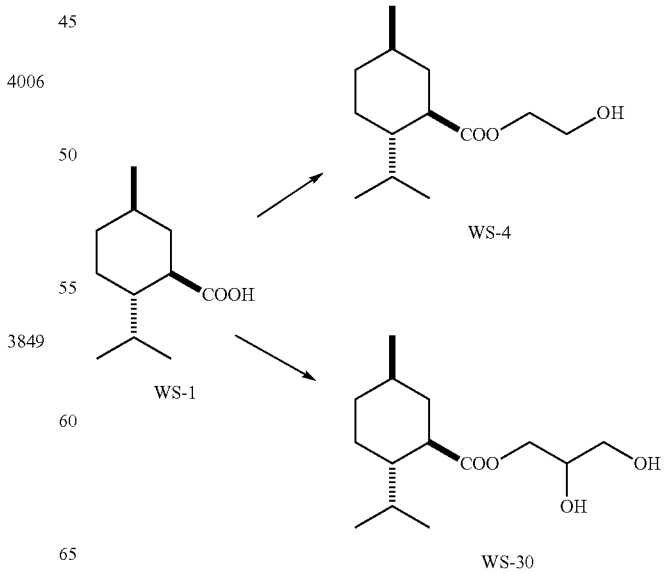

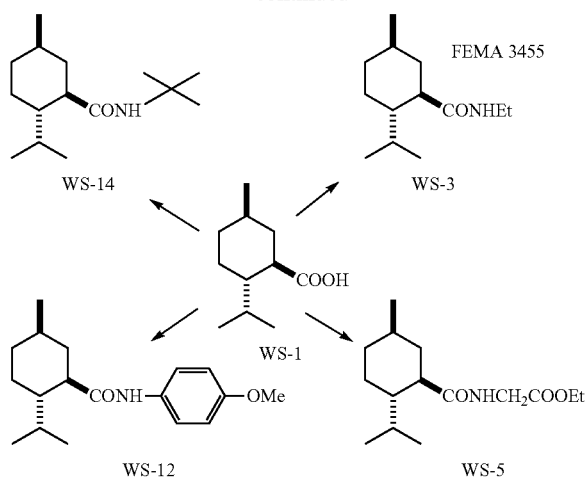

The esters derived from WS-4 are described in, for example, U.S. Pat. No. 4,157,384, and the corresponding N-substituted amides in J. Soc. Cosmet. Chem. S. 185-200 (1978).

Acyclic Carboxamide Compounds

Preferred acyclic carboxamides are derived from the following structure:

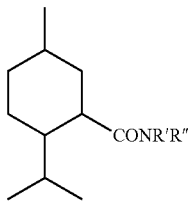

(Formula I)

wherein R' and R" may be, irrespective of each other, hydrogen, a hydroxyl group or an alkyl radical having up to 25 C-atoms, an aryl group having, up to 10 C-atoms, selected from substituted and unsubstituted phenyl-, phenylalkyl-, naphthyl- and pyridyl radicals. The alkyl radical may be branched, unbranched or even cyclical, thus covering alkyl-, cycloalkyl-, alkenyl-, cycloalkenyl-, alkynyl-, hydroxyalkyl-, acyloxyalkyl-, alkoxy-, alkoxyalkyl-, aminoalkyl, acylaminoalkyl-, carboxyalkyl radicals, and similar combinations.

Preferably R' and R" are methyl, ethyl, propyl, butyl, isobutyl, n-decyl, cyclopropyl, cyclohexyl, cyclopentyl, cycloheptylmethyl, 2-hydroxyethyl, 3-hydroxy-n-propyl, 6-hydroxy-n-hexyl, 2-aminoethyl, 2-acetoxyethyl, 2-ethylcarboxyethyl, 4-hydroxybut-2-ynyl, carboxymethyl, benzyl, naphthyl, 4-methoxyphenyl, 4-hydroxyphenyl, 4-methylphenyl, 3-hydroxy-4-methylphenyl, 4-fluorophenyl, 4-nitrophenyl, 2-hydroxynaphthyl or pyridyl.

It is particularly preferable for the cooling agent to be A (1R,2S,5R)-N-(4-methoxyphenyl)-5-methyl-2-(1-methylethyl)cyclohexane-carboxamide (FEMA 4681), which has the following structure (II):

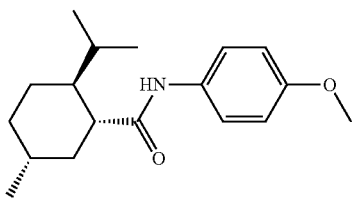

(Formula II)

Alcohol B

Suitable compounds for alcohol (B) are those selected from the group consisting of C1 to C3 alcohols or mixtures thereof, such as methanol, ethanol, propanol or 1,2-Propanediol. Ethanol and 1,2-Propanediol are particularly preferable.

Hydrophobic Compound C

Suitable hydrophobic compounds (C) are selected from the group consisting of essential oil (natural oils), neutral oils and vegetable oils.

Preferred ethereal oils are selected from the group consisting of peppermint oil (menthol), carvone, eucalyptus oil, grapefruit, orange oil, citrus oil, oil of turpentine, tea tree- and clove oil, camphor, rose oil, lavender oil or methyl salicylate or mixtures thereof.

Preferred vegetable oils are oil-seed-derived fats and oils selected from the group consisting of sunflower-, olive-, safflower oil, sesame and almond oil, alginic oil, apricot kernel oil, argan oil, avocado oil, borage oil or borage seed oil, cashew skin oil, rosehip kernel oil, hazelnut oil, jojoba oil, coffee bean oil, camomile oil, macadamia oil, almond oil, papaya seed oil, pistachio oil, castor oil, sandthorn oil, sandthorn seed oil, walnut oil or mixtures thereof.

Preferred neutral oils (MCT oil=medium chain triglycerides) are mixtures of medium chain fatty acids (triglycerides), or more precisely a mixture of capric acid and caprylic acid (CAS number 73398-61-5).

Palm kernel or coconut butter oils are the basis for producing neutral oils. The fats are saponified (split by hydrolysis), unwanted fatty acids (incl. lauric acid, myristic acid) are separated off and the wanted fatty acids are reesterified with glycerol. MCTs are commercially available under such trade names as Mygliol 812 from Sasol, Myritol 312® from Cognis and Tegosoft® CT from Evonik. The various products differ in terms of the percentage composition of the two fatty acids, capric acid and caprylic acid. All are lipids based on approximately 50-65% caprylic acid (C8:0) and approximately 30-45% capric acid (C10:0); capronic acid (C6:0), lauric acid (C12:0) and myristic acid (0.4:0) are present in very small amounts.

Production Method

The cooling composition is produced in a spray-granulation process in which the cooling agent (A), alcohol (B) and hydrophobic compound (C) components are encapsulated. It is important in this process that the cooling agent (A) is completely dissolved in an upstream step in (B) and (C), so that a homogeneous mixture is produced, the temperature being kept at 40° C. to 100° C., for complete dissolution of (A). All the components are then encapsulated in a spray-granulation treatment process, in which the temperature should then be kept at 35° C. to 65° C., preferably at 38° C. to 60° C., more preferably at 39° C. to 43° C., in order to prevent the cooling agent (A) from recrystallising. The granulate particles obtained from the spray granulation have an average particle size of 0.3 mm to 0.9 mm, preferably of 0.4 mm to 0.8 mm, more preferably of 0.5 mm to 0.6 mm.

When producing the cooling composition, it is particularly important to ensure that the cooling agent (A) is completely dissolved. This is achieved on the one hand on account of the temperature and on the other hand on account of the special combination of (A), (B) and (C). Preferably, (A) is dissolved at 40° C. to 100° C., preferably at 45° C. to 80° C., more preferably at 50° C. to 70° C. and even more preferably at 40° C. to 50° C.

It is also essential for the temperature in the subsequent spray-granulation process to be kept so as to prevent the cooling agent (A) from recrystalising, i.e. the temperature is kept at 35° C. to 65° C., preferably at 38° C. to 60° C., more preferably at 40° C. to 43° C.

In a preferred embodiment, the cooling agent (A) is (1R,2S,5R)-N-(4-methoxyphenyl)-5-methyl-2-(1-methylethyl)cyclohexane-carboxamide (FEMA 4681), the alcohol (B) is ethanol and the hydrophobic compound is (C) neutral oil.

In a preferred embodiment, the cooling agent (A) is (1R,2R,5R)-N-(4-methoxyphenyl)-5-methyl-2-(1-methylethyl)cyclohexane-carboxamide (FEMA 4681), the alcohol (B) is 1,2-propanediol and the hydrophobic compound (C) is neutral oil.

In a preferred embodiment, the cooling agent (A) is (1R,2R,5R)-N-(4-methoxyphenyl)-5-methyl-2-(1-methylethyl)cyclohexane-carboxamide (FEMA 4681), the alcohol (B) is ethanol and the hydrophobic compound (C) is peppermint oil.

In these combinations, the cooling composition can be incorporated particularly well into a chewing gum or sweet and the other above-described advantages of the invention emerge particularly clearly. In particular, these special combinations actually allow a physiological cooling effect in the chewing gum or sweets to be perceived upon consumption.

The fluidised bed spray granulation allows active substances to be encapsulated in compact and virtually round granulates having excellent physical properties. The process is well known in the prior art and is described at length in, for example, EP1139791. In fluidised bed spray granulation, solid-containing fluids (such as suspensions or emulsions) are atomised in the fluidised bed and encounter the granulation seeds in drop form. The fluid thus evaporates and the solid is applied to the granulation seeds, forming a solid coating. This is repeated continuously in the fluidised bed so that very compact granulates, built up in a shell-like manner, are produced. Parameters such as grain size, residual moisture and solid content can be set with a high degree of precision with fluidised bed spray granulation, and therefore the most diverse of substances can be processed to form granulates. Since the drying and shaping processes run simultaneously with granulation in fluidised bed methods, fluidised bed spray drying granulation can be said to be continuous (M. J. V. Goldschmidt, G. G. C. Weijersa, R. Boerefijn, J. A. M. Kuipers: "Discrete element modelling of fluidised bed spray granulation", Powder Technology 138 (2003) 39-45; Maksym Dosta, Stefan Heinrich, Joachim Werther: Fluidized bed spray granulation: "Analysis of the system behaviour by means of dynamic flowsheet simulation", Powder Technology 204 (2010) 71-82).

Therefore, the invention also relates to a granulate containing cooling agent (A), alcohol (B) and hydrophobic compound (C), which can be obtained using the above-described spray-granulation method.

In a preferred embodiment, a granulate according to the invention has the following composition:

| Composition | | D | E |
|---|---|---|---|
| Mixture A | Modified starch | 45-60 | 45-60 |
| | Acacia gum (Senegal) | 15-25 | 15-25 |
| | Sugar alcohol | 5-10 | 5-10 |
| | Colourant | 0-2 | 0-2 |
| | Polysaccharide | 0-2 | 0-2 |
| | Gelling agent* | 0-2 | 0-2 |
| | Maltodextrin | — | 50-75 |
| Mixture B | Cooling composition according to the invention | 10-30 | 10-30 |

In a preferred embodiment, a granulate according to the invention contains the following composition:

| Composition | | D | E |
|---|---|---|---|
| Mixture A | Modified starch | 50.0 | 50.0 |
| | Acacia gum (Senegal) | 20.0 | 20.0 |
| | Sugar alcohol | 7.0 | 7.0 |
| | Colourant | — | 0.15 |
| | Polysaccharide | — | 1.5 |
| | Gelling agent * | — | 1.0 |
| | Maltodextrin | — | 68.0 |
| Mixture B | Cooling composition according to the invention | 20.0 | 20.0 |

INDUSTRIAL APPLICABILITY

Chewing Gum

A preferred oral preparation incorporating the cooling composition is chewing gum.

The expression "chewing gum" used here covers in particular sugar-coated chewing gum, chewing gum strips, chewing gum pellets, chewing gum candies and chewing gum squares, as well as bubble gum and the like.

The preferred oral preparation incorporating the cooling preparation according to the invention is chewing gum. Such a preparation preferably comprises a) 5-95 wt. % chewing gum base, b) 5-95 wt. % filler and sweetener, c) 0.1-15 wt. % flavouring agents and d) 0.4-2 wt. % cooling composition according to the invention. In the oral preparations used, in particular in chewing guns or sweets, the cooling preparation according to the invention provides a physiological cooling effect, giving the consumer the impression of long-lasting freshness.

Water-Insoluble Base

The water-insoluble base, which is also referred to as the "gum base", conventionally comprises natural or synthetic elastomers, resins, fats and oils, emollients, fillers, colourants and optionally waxes. The base content in the total composition conventionally accounts for 5 to 95, preferably 10 to 50 and in particular 20 to 35 wt. %. In a typical embodiment of the invention, the base is composed of 20 to 60 wt. % synthetic elastomers, 0 to 30 wt. % natural elastomers, 5 to 55 wt. % emollients, 4 to 35 wt. % fillers and, in smaller amounts, additives such as colourants, antioxidants and the like, with the proviso that they are at best water-soluble in small amounts.

As regards suitable synthetic elastomers, examples include polyisobutylene having an average molecular weight (according to GPC) of 10,000 to 100,000 and preferably 50,000 to 80,000, isobutylene-isoprene-copolymers ("butyl elastomers"), styrol-butadiene-copolymers (styrol: butadiene ratio e.g. 1:3 to 3:1), polyvinylacetate having an average molecular weight (according to GPC) of 2,000 to 90,000 and preferably 10,000 to 65,000, polyisoprene, polyethylene, vinylacetate-vinyllaurate-copolymers and mixtures thereof. Examples of suitable natural elastomers are natural rubbers, such as smoked or liquid latex or guayule, and natural rubber materials, such as jelutong, lechi caspi, perillo, sorva, massaranduba balata, massaranduba chocolate, nispero, rosindinba, chicle, gutta hang lkang and mixtures thereof. The choice of synthetic and natural elastomers and the mixing ratios thereof is based mainly on whether or not the intention is to create bubbles with the chewing gum ("bubble gum"). Preferably, the elastomer mixtures used contain jelutong, chicle, sorva and massaranduba.

Mostly, when processed, the elastomers prove to be too rigid or insufficiently deformable. It has therefore proven to be advantageous to also use special emollients which, of course, particularly also need to meet all the requirements for approval as food additives. In this regard, esters of resin acids are considered, such as esters of lower aliphatic alcohols or polyols having fully or partly hydrogenated monomeric or oligomeric resin acids. In particular, methyl, glycerol or pentaerythritol esters or mixtures thereof are used for this purpose. Alternatively, terpene resins, which may be derived from α-pinene, β-pinene, δ-limonene or mixtures thereof, are further possibilities.

Possible fillers or texturisers include magnesium or calcium carbonate, ground pumice stone, silicates, particularly magnesium or aluminium silicates, clays, aluminium oxides, talcum, titanium dioxide, mono-, di- and tricalcium phosphate and cellulose polymers.

Suitable emulsifiers are tallow, hydrogenated tallow, hydrogenated or partly hydrogenated vegetable oils, cocoa butter, partial glycerides, lecithin, triacetin and saturated or unsaturated fatty acids containing 6 to 22 and preferably 12 to 18 carbon atoms and mixtures thereof.

Examples of possible fillers and whiteners include the FD & C types, plant and fruit extracts permitted for colouring foods, and titanium dioxide.

The base masses may contain waxes or be wax-free. Examples of wax-free compositions can be found, inter alia, in patent specification U.S. Pat. No. 5,286,500, to the content of which reference is expressly hereby made.

Water-Soluble Components

In addition to the water-insoluble gum base, chewing gum preparations often contain a water-soluble component, which is formed, for example, by softeners, sweeteners, fillers, flavouring agents, flavour enhancers, emulsifiers, colourants, acidifiers, antioxidants and the like, with the proviso in this case that the constituents have at least adequate solubility in water. Accordingly, individual constituents may belong both to the water-insoluble phase and to the water-soluble phase, depending on the water solubility of the particular agents. However, combinations may also be used, for example, a combination of a water-soluble and a water-insoluble emulsifier, the individual agents being in different phases. The water-insoluble component conventionally accounts for 5 to 95 wt. % and preferably 20 to 80 wt. % of the preparation.

Water-soluble softeners or plasticisers are added to the chewing gum compositions to improve chewability and the chewing feel and are present in the mixtures in amounts of typically 0.5 to 15 wt. %. Typical examples are glycerol, lecithin and aqueous solutions of sorbitol, hydrogenated starch hydrolysates or corn syrup.

As regards suitable sweeteners, both sugar-containing and sugar-free compounds are possibilities and used in amounts of 5 to 95 wt. %, preferably in amounts of 20 to 80 wt. % and in particular in amounts of 30 to 60 wt. %, based on the chewing gum composition. Typical saccharide sweeteners are sucrose, dextrose, maltose, dextrin, dried invert sugar, fructose, levulose, galactose, corn syrup and mixtures thereof. As regards sugar substitutes, sorbitol, mannitol, xylitol, hydrogenated starch hydrolysates, maltitol and mixtures thereof can be considered. Other possible additives include what are known as high-intensity artificial sweeteners (HIAS) such as, for example, sucralose, aspartame, acesulfame salts, alitame, saccharin and saccharin salts, cyclamic acid and salts thereof, glycyrrhizins, dihydrochalcones, thaumatin, monellin and the like, either individually or in mixtures. The hydrophobic HIAS, which form the subject matter of international patent application WO 2002 091849 A1 (Wrigleys), are also particularly effective, as are *Stevia* extracts and their active components, particularly, rebaudioside A. The amount of these substances which is used is determined primarily by their capacity and is typically in the range of 0.02 to 8 wt. %.

Fillers such as polydextrose, raftilose, raftilin, fructo-oligosaccharides (NutraFlora), palatinose oligosaccharides, guar gum hydrolysates (Sun Fiber) and dextrins (Fibersol) are particularly suited to the production of low-calorie chewing gum.

The choice of additional flavouring agents is virtually limitless and is not critical to the essence of the invention. Conventionally, the total content of all flavouring agents is 0.1 to 15 and preferably 0.2 to 5 wt % based on the chewing gum composition. Examples of other suitable flavouring agents are essential oils, aromas and the like, such as mint oil, spearmint oil, aniseed oil, star anise oil, caraway oil, eucalyptus oil, fennel oil, citrus oil, wintergreen oil, clove oil and the like, as they are used, for example, in oral and dental care products.

Chewing gum may additionally contain auxiliary agents and additives, which are suitable, for example, for dental care, more particularly for fighting plaque and gingivitis, such as chlorhexidine, CPC or triclosan. It may also contain pH adjusters (for example, buffer or urea), anti-caries agents (for example, phosphates or fluorides), biogenic active substances (antibodies, enzymes, caffeine, plant extracts), provided that these substances are permitted in foods and do not undesirably interact with one another.

Correspondingly, the invention also relates to a method for producing chewing gum with longer-lasting freshness, comprising:
  i) producing a chewing gum composition having 5-95 wt. % chewing gum base, 5-95 wt. % filler and sweetener, 0.1-15 wt. % flavouring agents; and
  ii) adding 0.2-3 wt. % cooling composition according to the invention which provides a physiological cooling effect for imparting freshness in the used preparations.

A concentration of 0.4-1 wt % cooling composition according to the invention is particularly effective.

Sweets

Another preferred oral preparation incorporating the cooling composition is a sweet.

As a sweet base, sweets mostly comprise sugar compounds, such as mono-, i- and trisaccharides, oligosaccharides or derivatives thereof, such as glucose, lactose, maltose, xylose, sucrose and fruit-oligosaccharides. In this case, a sweet base contains 10 to 99 wt. %, preferably 15 to 95 wt. %, more preferably 15 to 95 wt. % sugar compounds.

Furthermore, sweets contain edible acids, such as aliphatic, saturated and unsaturated mono-, di- and tricarbonic acids, such as citric acid, fumaric acid, maleic acid, lactic acid, tartaric acid, adipic acid, succinic acid, ascorbic acid, glutaric acid, acetic acid, phosphoric acid, etc.

Sweets (including drops) come in almost every conceivable colour, flavour and shape, mostly being elliptical or spherical. Generally, sweets have a particularly sweet, sour or liquid filling. A distinction is made between hard sweets, having a glass-like design and a water content of up to 3%, and soft sweets (such as toffee), which are chewy, have a chewing-gum-like consistency and contain up to 8% water.

Sweets of the present invention preferably have a filling comprising the cooling composition according to the invention. These sweets preferably have a sweet base of 60-95 wt. %, more preferably 75 to 85 wt. % and a filling of 5 to 40 wt. %, preferably 15 to 25 wt. %. In this case, there are other ingredients in the filling in addition to the cooling composition. Such a sweet contains the cooling composition in an amount of 0.2 to 4 wt. %, preferably 0.5 to 2 wt. %.

The filling of such a sweet may be solid, powdery, aqueous, viscous, gel-like or rubbery. Most aqueous fillings have a water content of less than 10%, preferably less than 8%, more preferably less than 6%.

The filling may also contain edible ingredients approved for the food industry, such as alcohols and polyalcohols, like glycerol, polyethylene glycol or propylene glycols having low molecular weights (less than 1000 MW). These are contained in the filling in the range of 30-95 wt %, preferably 40 to 90 wt. %, more preferably 40 to 60 wt. %.

Furthermore, sweet fillings can contain sweeteners in an amount of 5 to 80 wt. %, preferably 30 to 75 wt. %. The sweeteners used in sweets can be taken from the section on chewing gum, since they are similarly applicable to sweets.

Sweet fillings also comprise thickening agents approved for the food industry, such as xanthan gum, carrageenan and derivatives thereof, hydroxylpropylmethylcellulose, sclerotium gum, pullulan, rhamsan gum, welan gum, konjac, curdlan, carbomer, algin, alginic acid, alginate and derivatives thereof, hydroxyethylcellulose and derivatives thereof, hydroxypropylcellulose and derivatives thereof, phosphate starch derivatives, guar gum and derivatives thereof, starch and derivatives thereof, copolymers of maleic anhydride having alkenes and derivatives thereof, ethylene glycol/propylene glycol copolymers, long chain alcohols, such as behenyl alcohol, poloxamers and derivatives thereof, polyacyrolate and derivatives thereof, methylcellulose and derivatives thereof, ethylcellulose and derivatives thereof, agar and derivatives thereof, pectin and derivatives thereof, chitosan and derivatives thereof, and high-molecular polyethylene glycols such as polyethylene glycols (having 10,000 MW or above), karaya gum, copolymers of vinylpyrrolidones having alkenes, polyacrylamides, chitin derivates, gelatine, beta-glucan, dextrin, dextran, cyclodextrin, methacrylate, microcrystalline cellulose, polyquats, furcellaran gum, ghatti gum, psyllium gum, quince gum, tamarind gum, larch gum, tara gum, tallow, kaolinic clay, bentonites, cellulose, fumed silica, and mixtures thereof.

Sweets preferably contain thickening agents in an amount of 0.001 to 10 wt. %, more preferably 0.01 to 5 wt. %, even more preferably 0.01 to 2.5 wt. % and most preferably 0.01 to 1 wt. %.

Aromatic substances may be either aqueous or oil-based and obtained for example from plant parts, such as leaves, blooms, fruits, etc. Suitable aromatic substances are derived, for example, from the oils of citrus fruits, oranges, bananas, grapes, lime, apricot, grapefruit or from the fruit of an apple, strawberries, cherries, oranges, pineapple or the aromas of coffee, cocoa, cola, peanut, almond, liquorice root or ginger root. Aromatic substances are used in sweets in an amount of preferably up to 4 wt %, more preferably of 0.1 to 1 wt. %.

Use of Preparations

Finally the invention further relates to the use of the cooling composition in order to impart freshness in the oral preparations due to a physiological cooling effect. The oral preparation is preferably a chewing gum or a sweet.

EXAMPLES

All percentages are given by weight unless indicated otherwise.

I) Production of Granulate Particles Having a Cooling Composition According to the Invention A mixture B is provided, heated to a temperature of 50° C. and stirred until a homogenous mixture is produced. Then, a carrier component made of a homogeneous mixture A is provided and also heated to 50° C., The mixture B is then dispersed into the carrier component mixture A and the entire mixture is spray-granulated, the temperature being kept at 39° C. to 40° C. throughout the process.

The granulate particles obtained from the spray-granulation may have an average particle size of 0.3 mm, 0.4 mm, 0.5 mm, 0.6 mm, 0.7 mm, 0.8 mm and 0.9 mm, depending on procedural conditions.

The granulate particles produced have the composition set out in table 1.

TABLE 1

Granulate containing a cooling composition

| Composition | | D | E |
|---|---|---|---|
| Mixture A | Modified starch | 45-60 | 45-60 |
| | Acacia gum (Senegal) | 15-25 | 15-25 |
| | Sugar alcohol | 5-10 | 5-10 |
| | Colourant | 0-2 | 0-2 |
| | Polysaccharide | 0-2 | 0-2 |
| | Gelling agent * | 0-2 | 0-2 |
| | Maltodextrin | — | 50-75 |
| Mixture B | Cooling composition according to the invention | 10-30 | 10-30 |

* pectin

Cooling compositions according to the invention may be composed as follows:

TABLE 2

Cooling composition

| Composition | F1 | F2 | F3 | F4[i)] | F5 | F6 | F7 | F8 |
|---|---|---|---|---|---|---|---|---|
| Cooling agent (A)* | 10.0 | 10.0 | 10.0 | 10.0 | 10.0 | 15.0 | 10.0 | 10.0 |
| Alcohol (B)** | — | 10.0 | 15.0 | 30.0 | 90.0 | 85.0 | 20.0 | 15.0 |
| Hydrophobic compound (C)*** | 90.0 | 80.0 | 75.0 | 60.0 | — | — | 70.0 | 75.0 |

*Cooling agent A selected from menthone glyceryl acetal (FEMA GRAS[i] 3807), menthone glyceryl ketal (FEMA GRAS 3808), menthyl lactate (FEMA GRAS 3748), menthol ethylene glycol carbonate (FEMA GRAS 3805), menthol propylene gycol carbonate (FEMA GRAS 3806), menthoxy-1,2-propanediol (FEMA GRAS 3784), menthoxy-2-methyl-1,2-propanediol (FEMA GRAS 3849) or (1R,2S,5R)-N-(4-methoxyphenyl)-5-methyl-2-(1-methylethyl) cyclohexane-carboxamide (FEMA 4681).
**Alcohol B: ethanol or 1,2-propanediol
***Hydrophobic compounds selected from: peppermint oil (menthol), carvone or neutral oils
[i)]Cooling agent A: (1R,2S,5R)-N-(4-methoxyphenyl)-5-methyl-2-(1-methylethyl) cyclohexane-carboxamide (FEMA 4681), alcohol B: ethanol, hydrophobic compound C: peppermint oil.

II) Chewing Gum Mass

A granulate according to table 1 and a chewing gum mass, as indicated in table 3 below, were used to produced chewing gum and the cooling effect thereof was assessed on a sensory basis.

TABLE 3

| Chewing gum masses | | | |
|---|---|---|---|
| Composition | K | L | M |
| Polyisobutylene (MW 20,000) | 20.0 | 25.0 | 30.0 |
| Sorbitol | 51.0 | 47.5 | 44.5 |
| Mannitol | 5.0 | 4.3 | 3.6 |
| Glycerol | 8.0 | 8.0 | 7.0 |
| Lycasin:Glycerin (1:1) | 8.2 | 8.0 | 7.0 |
| Lecithin | 0.2 | 0.2 | 0.2 |
| Aromatic mixture | 1.0 | 1.0 | 1.0 |
| Water | | from 100 | |

III) Sensory Test

The cooling compositions according to the invention were incorporated into chewing gum masses. The cooling effect of the chewing gum was then tested on a sensory basis by trained people. The sensory assessment is summarised in table 4 and the following rating system was used:
 Assessment range 0: no perceivable cooling effect
 Assessment range 1-3: weak cooling effect
 Assessment range 4-6: average cooling effect
 Assessment range 7-8: strong cooling effect
 Assessment range 9-10: very strong cooling effect
Examples E1 to E4 conform with the invention. Example V1 can be used for comparison.

TABLE 4

| Sensory assessments of chewing gum with or without cooling composition | | | | | |
|---|---|---|---|---|---|
| Time [min] | V1 | E1 | E2 | E3 | E4 |
| 1 | 1-3 | 1-3 | 4-6 | 4-6 | 4-6 |
| 2 | 4-6 | 4-6 | 7-8 | | |
| 3 | | | | | |
| 4 | 7-8 | | 9-10 | | 9-10 |
| 5 | | | | 7-8 | |
| 6 | 9-10 | | | | 7-8 |
| 7 | | | | | |
| 8 | | | | | |
| 9 | | | | | |
| 10 | | | | 4-6 | |
| 15 | | | 4-6 | | 4-6 |
| 20 | | | | | |
| 25 | 4-6 | 1-3 | | | |
| 30 | | | | 1-3 | 1-3 |
| 35 | | | | | |
| 40 | | | | | |
| 45 | | | 1-3 | | |

Referring to V1, we will briefly explain how the table should be interpreted: A weak cooling effect can be perceived in the first minute. This increases over the period from the second to the third minute, entering the average cooling effect range. In the fourth to the fifth minute, the product shows a strong cooling effect, which increases further in the sixth minute to form an organoleptic, very strong cooling effect, which drops off sharply in the twenty-fifth minute to form an average cooling effect.

The control formulation V1 is a standard mixture having citrus mint and was used as a benchmark.
 E1: 0.4% granulate 0 in a chewing gum mass according to table 3
 E2: 0.6% granulate 0 in a chewing gum mass according to table 3
 E3: 0.4% granulate E in a chewing gum mass according to table 3
 E4: 0.6% granulate E in a chewing gum mass according to table 3

If the cooling agent (A) is incorporated simply into sugar alcohol and not, as according to the invention, by means of spray-granulation, but is merely melted therein and then formulated into a chewing gum mass, no cooling effect materialises, as shown in table 5:

TABLE 5

| Chewing gum mass having a cooling composition incorporated without spray-granulation | | | |
|---|---|---|---|
| Comparative test | V1 | V2 | V3 |
| Cooling agent in isomalt | 1% | 10% | 10% |
| Isomalt having cooling agent in chewing gum | 0.4% | 0.2% | 0.8% |
| Addition of dummy* | 1.2% | 1.2% | 1.2 |
| Sensory test | | No cooling | |

*1 part triacetin and 2 parts MCT-vegetable oil

The following table 6 gives an example of a sweet formulation:

TABLE 6

| Sweet containing a cooling composition | |
|---|---|
| Composition | A |
| Sucrose | 59.8 |
| Glucose (liq.) | 43.7 |
| Water | 16.2 |
| Citric acid anhydride | 1.2 |
| Cooling composition according to the invention | 0.3 |
| Aroma | 0.2 |

The invention claimed is:

1. A method for producing granulate particles that provide a cooling effect to oral preparations comprising:
 (I) obtaining a carrier mixture (A);
 (II) mixing (a), (b), and (c) at a temperature of 40° C. to 100° C. to form a homogenous mixture (B), wherein (a) is completely dissolved in the homogenous mixture (B), wherein mixture (B) comprises:
  (a) 2 to 15 wt. %, based on the total weight of the mixture (B) of a cooling agent selected from the group the group consisting of:
   menthone glyceryl acetal (FEMA GRAS 3807),
   menthone glyceryl ketal (FEMA GRAS 3808),
   menthyl lactate (FEMA GRAS 3748),
   menthol ethylene glycol carbonate (FEMA GRAS 3805),
   menthol propylene gycol carbonate (FEMA GRAS 3806),
   menthoxy-1,2-propanediol (FEMA GRAS 3784),
   menthoxy-2-methyl-1,2-propanediol (FEMA GRAS 3849), and
   (1R,2S,5R)-N-(4-methoxyphenyl)-5-methyl-2-(1-methylethyl) cyclohexane-carboxamide (FEMA 4681);
  (b) 10 to 35 wt. %, based on the total weight of the mixture (B), of an alcohol selected from the group consisting of ethanol and 1,2-propanediol; and
  (c) 60 to 80 wt. %, based on the total weight of the mixture (B), of peppermint oil, carvone, or a neutral oil having a content of 50-65% caprylic acid and 30-45% capric acid;

(III) dispersing the homogenous mixture (B) into the carrier mixture (A) and forming a final mixture for spray granulating;

(IV) spray granulating the final mixture; and (V) obtaining granulate particles having an average particle size of 0.3 mm to 0.9 mm;

wherein the granulate particles comprise 10 to 30 wt. % of components from mixture (B), based on the total weight of the granulate particles.

2. The method of claim 1, wherein the spray granulating of the final mixture of (IV) is carried out at a temperature of 35° C. to 100° C.

3. A granulate particle produced according to the method of claim 1.

4. A chewing gum comprising:
a) 5 to 95 wt. % of a chewing gum base;
b) 5 to 95 wt. % of a filler and a sweetener; and
c) 0.1 to 15 wt. % of flavoring agents; and
d) 0.4 to 2 wt. % of granulate particles of claim 3.

5. The chewing gum of claim 4, wherein the chewing gum base comprises:
i) 20 to 60 wt. % synthetic elastomers;
ii) 0 to 30 wt. % natural elastomers;
iii) 5 to 55 wt. % emollients; and
iv) 4 to 35 wt. % fillers.

6. A hard or soft sweet comprising:
a) 10 to 99 wt. % of a sugar compound;
b) 0.001 to 10 wt. % of a thickening agent; and
c) up to 8% water; and
d) granulate particles of claim 3.

7. The hard or soft sweet of claim 6 wherein the sugar compound is sucrose.

8. The method of claim 1, wherein the carrier mixture A comprises modified starch.

9. The method of claim 8, wherein the granulate particles comprise 45 to 60 wt. % of modified starch.

10. The method of claim 1, wherein (a), (b), and (c) are mixed at a temperature of 45° C. to 80° C.

11. The method of claim 1, wherein 2 to 10 wt. % of the cooling agent (a) is mixed with (b) and (c), based on the total weight of the mixture (B).

12. The method of claim 1, wherein 15 to 35 wt. % of the alcohol (b) is mixed with (a) and (c), based on the total weight of the mixture (B).

13. The method of claim 1, wherein the alcohol is ethanol.

14. The method of claim 1, wherein the cooling agent (a) is (1R,2S,5R)-N-(4-methoxyphenyl)-5-methyl-2-(1-methylethyl) cyclohexane-carboxamide (FEMA 4681).

15. The method of claim 1, wherein 60 to 80 wt. % of the peppermint oil (c) is mixed with (a) and (b), based on the total weight of the mixture (B).

16. A method for producing granulate particles that provide a cooling effect to oral preparations comprising:

(I) obtaining a carrier mixture (A) comprising modified starch;

(II) mixing (a), (b), and (c) at a temperature of 45° C. to 80° C. to form a homogenous mixture (B), wherein (a) is completely dissolved in the homogenous mixture (B), wherein mixture (B) comprises:

(a) 2 to 10 wt. %, based on the total weight of the mixture (B) of a cooling agent selected from the group the group consisting of:
menthone glyceryl acetal (FEMA GRAS 3807),
menthone glyceryl ketal (FEMA GRAS 3808),
menthyl lactate (FEMA GRAS 3748),
menthol ethylene glycol carbonate (FEMA GRAS 3805),
menthol propylene gycol carbonate (FEMA GRAS 3806),
menthoxy-1,2-propanediol (FEMA GRAS 3784),
menthoxy-2-methyl-1,2-propanediol (FEMA GRAS 3849), and
(1R,2S,5R)-N-(4-methoxyphenyl)-5-methyl-2-(1-methylethyl) cyclohexane-carboxamide (FEMA 4681);

(b) 15 to 35 wt. %, based on the total weight of the mixture (B), of ethanol; and (c) 60 to 80 wt. %, based on the total weight of the mixture (B), of peppermint oil, carvone, or a neutral oil having a content of 50-65% caprylic acid and 30-45% capric acid;

(III) dispersing the homogenous mixture (B) into the carrier mixture (A) and forming a final mixture for spray granulating;

(IV) spray granulating the final mixture; and (V) obtaining granulate particles having an average particle size of 0.3 mm to 0.9 mm;

wherein the granulate particles comprise 45 to 60 wt. % of modified starch and 10 to 30 wt. % of components from mixture (B), based on the total weight of the granulate particles.

17. The method of claim 16, wherein the cooling agent (a) is (1R,2S,5R)-N-(4-methoxyphenyl)-5-methyl-2-(1-methylethyl) cyclohexane-carboxamide (FEMA 4681).

18. A granulate particle produced according to the method of claim 16.

* * * * *